US00PP13256P2

(12) United States Plant Patent
Osiecki

(10) Patent No.: US PP13,256 P2
(45) Date of Patent: Nov. 19, 2002

(54) SPATHIPHYLLUM PLANT NAMED 'STHIRTYONE'

(75) Inventor: Marian Wincenty Osiecki, Marianna, FL (US)

(73) Assignee: Olgesby Plants International, Inc., Altha, FL (US)

( * ) Notice: Subject to any disclaimer, the term of this patent is extended or adjusted under 35 U.S.C. 154(b) by 0 days.

(21) Appl. No.: 09/931,534

(22) Filed: Aug. 17, 2001

(51) Int. Cl.[7] ..... A01H 5/00

(52) U.S. Cl. ..... Plt./364

(58) Field of Search ..... Plt./364

*Primary Examiner*—Bruce R. Campell
*Assistant Examiner*—Annette H. Para

(57) ABSTRACT

A new and distinct cultivar of Spathiphyllum is provided. It is a medium size plant, suitable for production in 15-cm to 25-cm containers, with moderately vigorous growth; symmetrical growth habit; wide, thick, exceptionally dark green and glossy leaves. Relatively large spathes with green veins on the back side are held at a moderate distance from foliage. No pollen observed.

3 Drawing Sheets

BOTANICAL CLASSIFICATION:

Spathiphyllum hybrid.

VARIETY DENOMINATION

'Sthirtyone'.

BACKGROUND OF THE INVENTION

This invention relates to a new and distinct cultivar of spathiphyllum plant, botanically known as Spathiphyllum hybrid, and hereinafter referred to by the cultivar name Sthirtyone.

The new cultivar is a product of a planned breeding program conducted by the Inventor in Altha, Fla. The objective of the program was to develop a Spathiphyllum cultivar useful for various container sizes with attractive growth habit and large, dark green and glossy leaves.

The new Spathiphyllum was discovered and selected by the Inventor in 1997 as a seedling within the progeny of a cross made in 1996 in a controlled environment in Altha, Fla. The female parent was a proprietary Spathiphyllum seedling selection identified by the code number 91-9-1. The male parent was a proprietary Spathiphyllum seedling selection identified by the code number 93-8-2. Both parental seedlings were obtained by the Inventor in the same breeding program in Altha and not patented.

Asexual propagation of 'Sthirtyone' since 1998 by means of tissue culture in Altha, Fla. has established that the unique characteristics of this new cultivar are in fact stable and reproduced true to type in successive generations.

SUMMARY OF THE INVENTION

The new Spathiphyllum cultivar has not been observed under all possible environmental conditions. The phenotype may vary somewhat with variations in environment and/or horticultural practices such as temperature, light intensity, day length, fertilization, irrigation, propagation procedures etc., without any variance in genotype.

The following traits have been repeatedly observed and in combination distinguish 'Sthirtyone' as a new and distinct cultivar of Spathiphyllum:

1. Medium size plant, appropriate for 15-cm to 25-cm containers;

2. symmetrical, rounded growth habit;

3. moderately vigorous growth;

4. large, wide, thick, exceptionally dark green and glossy leaf blades;

5. relatively large spathes with green veins on the back surface 6. lack of regular pollen production.

Plants of 'Sthirtyone' are distinguished from plants of the female parent, Spathiphyllum seedling 91-9-1, by its smaller size; more compact growth habit; less abundant branching and flowering; smaller leaves; thinner peduncles; spathes that are more elongated, not as pure white; and by the lack of regular pollen production.

Plants of 'Sthirtyone' are distinguished from plants of the male parent, Spathiphyllum seedling 93-8-2 by its smaller size; more compact and fuller growth habit; less abundant flowering; smaller, darker and glossier leaves; smaller spathes; and by the lack of regular pollen production.

The new cultivar can be compared to the known cultivars: Spathiphyllum 'Gorgusis No. 1', disclosed in U.S. Plant Pat. No. 6,964, a/k/a Sensation® and Spathiphyllum Supreme® (not patented). The comparisons were made on plants of the same age, grown side-by-side under the same greenhouse conditions in Altha, Fla.

Plants of the new Spathiphyllum cultivar differ from plants of Spathiphyllum Gorgusis No. 1 in the following characteristics:

1. Plants of 'Sthirtyone' are smaller, have more compact, fuller growth habit and are suitable for 15-cm to 25-cm containers, whereas plants of 'Gorgusis No. 1' are suitable for 25-cm and larger containers.

2. Plants of 'Sthirtyone' start flowering earlier than plants of 'Gorgusis No. 1'.

3. Leaves of 'Sthirtyone' have smaller and glossier leaf blades and shorter and thinner petioles than leaves of 'Gorgusis No. 1'.

4. Spathes of 'Sthirtyone' are smaller, have more yellow and green coloration and are held on shorter and thinner peduncles than spathes of 'Gorgusis No. 1'.

Plants of the new Spathiphyllum cultivar differ from plants of Spathiphyllum Supreme in the following characteristics:

1. Plants of 'Sthirtyone' are smaller, have more rounded, symmetrical and fuller growth habit than plants of Supreme.

2. Plants of 'Sthirtyone' branch and flower less readily than plants of Supreme.

3. Leaf blades of 'Sthirtyone' are shorter, with lower length; width ratio, darker green and glossier than leaf blades of Supreme.

4. Petioles of 'Sthirtyone' are shorter, thicker, have shorter and thicker geniculum and more prominent petiole wings than petioles of Supreme.

5. Spathes of 'Sthirtyone' are held closer to foliage on shorter peduncles than spathes of Supreme.

6. Spathes of 'Sthirtyone' are longer, with greater length: witdth ratio, oval with attenuate base, whereas spathes of Supreme are between broadly ovate, oval and orbicular with obtuse base.

7. Spathes of 'Sthirtyone' are not as pure white and have green veins on the back side, whereas green coloration on spathes of Supreme is limited to apex and midrib on the back side.

BRIEF DESCRIPTION OF THE PHOTOGRAPHS

The accompanying photographs illustrate the appearance of the new Spathiphyllum cultivar, showing the colors as true as it is reasonably possible in color reproductions of this type. Colors in the photographs may appear slightly different from the color values cited in the botanical description, which accurately describe the actual colors of the plants of the new cultivar. The plant of 'Sthirtyone' depicted in the photographs was approximately 15 months from planting a single tissue culture-produced microcutting, and was grown in a 15-cm container.

In the photographs:

BOTANICAL DESCRIPTION OF THE NEW CULTIVAR

Figure 1:
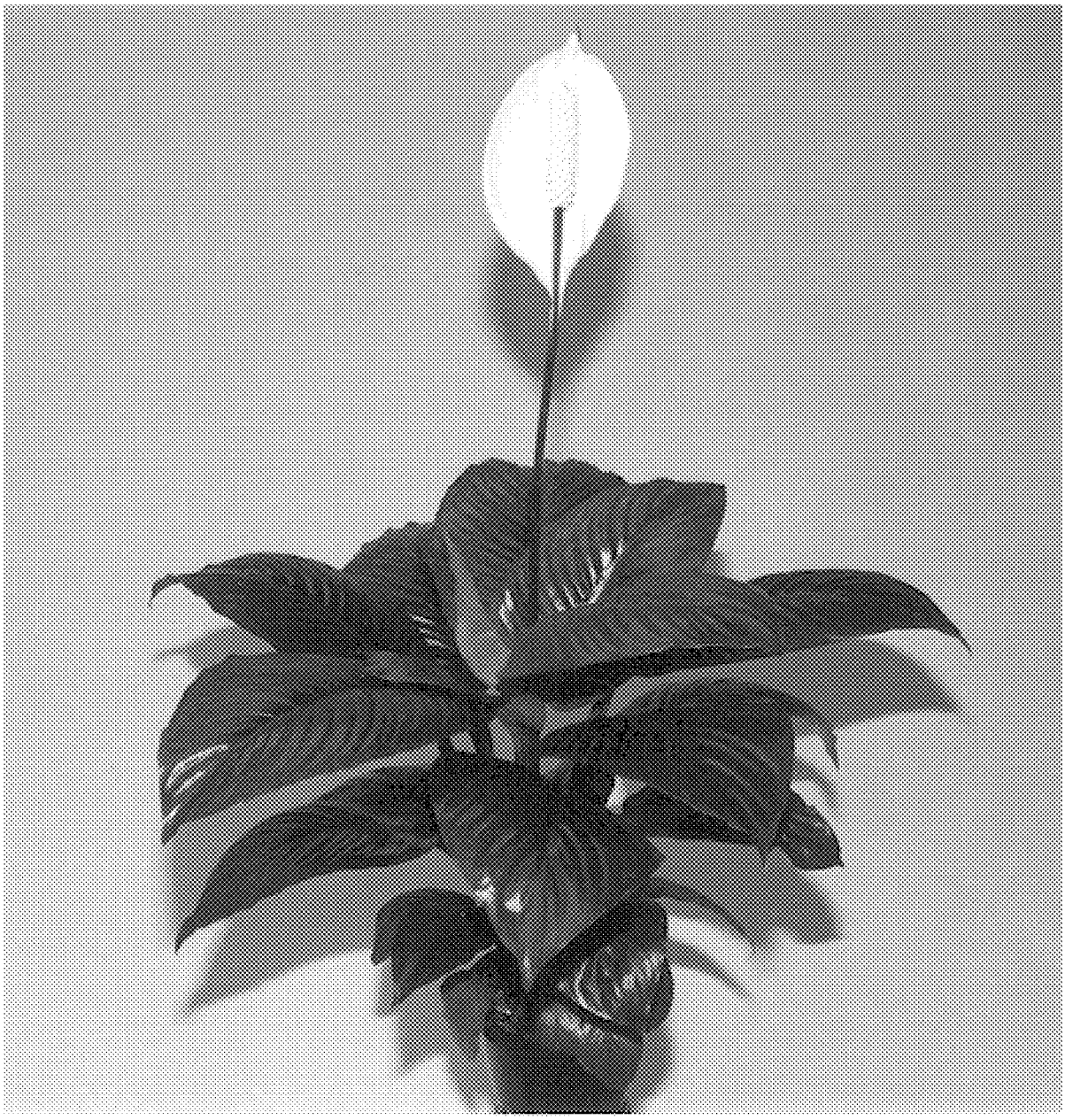
FIG. 1 depicts the whole plant.
Figure 2:
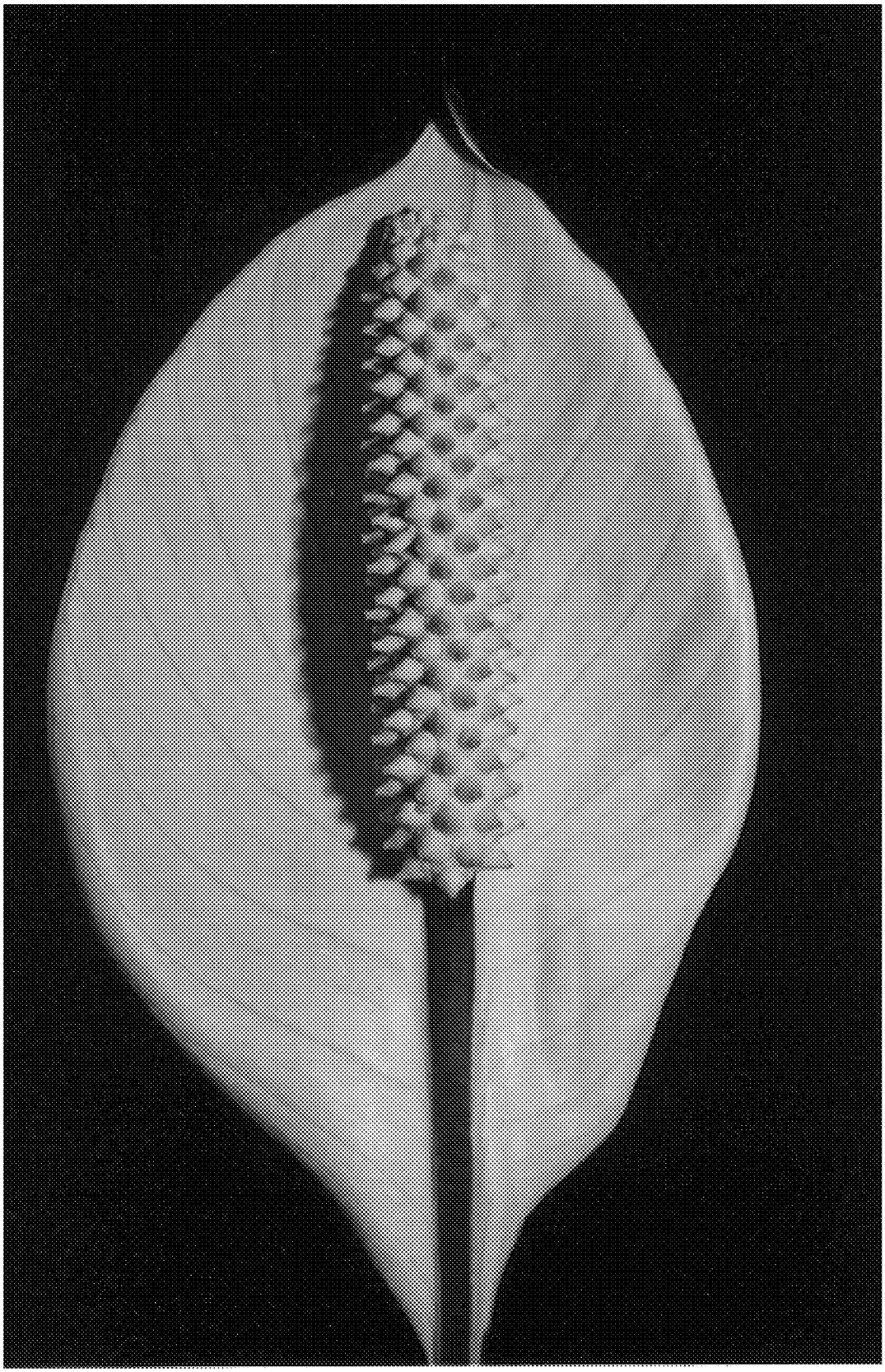
FIG. 2 illustrates the mature inflorescence.
Figure 3:
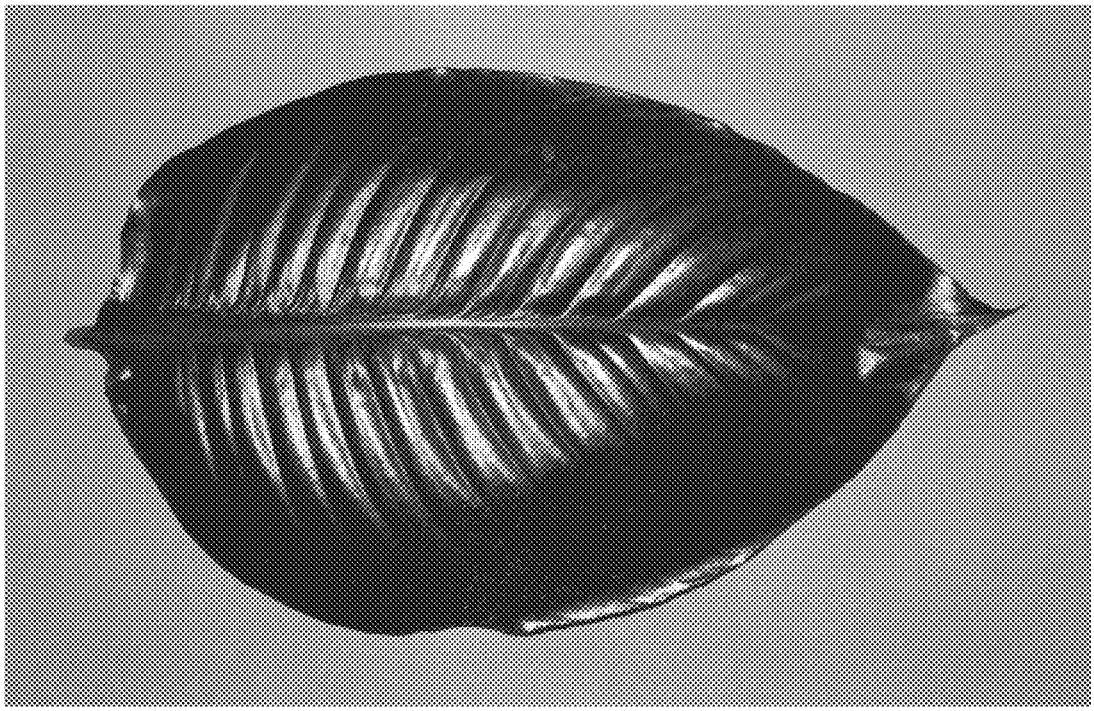
FIG. 3 illustrates the adaxial side of a mature leaf.
Figure 4:
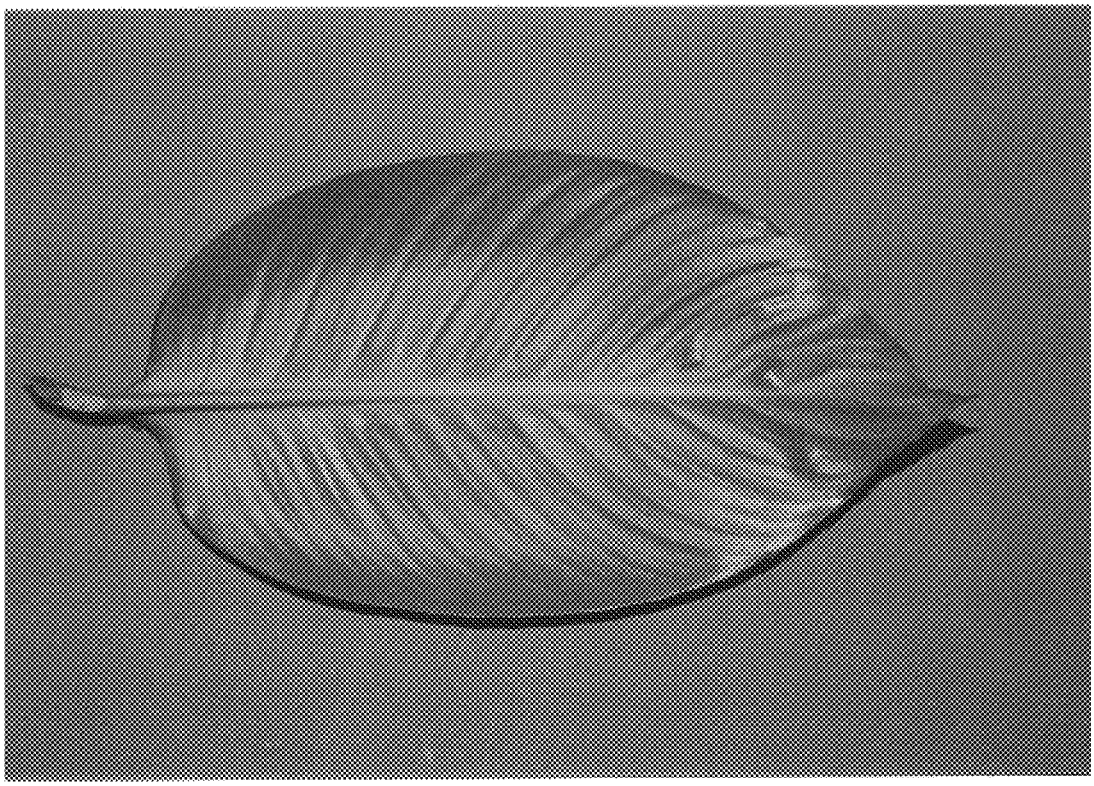
FIG. 4 illustrates the abaxial side of a mature leaf.

The following observations and measurements were recorded in January 2001 on plants grown in a polycarbonate-covered greenhouse in Altha, Fla. under conditions which closely approximate those used in commercial horticultural practice. During growth of these plants day temperature in the greenhouse ranged between 23° C. and 28° C., night temperature ranged between 20° C. and 23° C., and light level ranged between 800 and 1500 foot-candles. Plants used for these observations were grown as single plants in 15-cm containers and were about 15 months from planting tissue culture-produced microcuttings.

Mature, fully developed plant organs were used for the following observations and measurements unless otherwise indicated. Two leaves immediately preceding a leaf supporting an inflorescence were used for mature leaf description. Numerical measurements represent means from typical plants of 'Sthirtyone'. Color references are made to The R.H.S. Colour Chart, except where general color terms of ordinary significance are used. Color values were determined under natural light of approximately 1500 to 2000 foot-candles.

Botanical classification: Spathiphyllum hybrid cultivar Sthirtyone.

Parentage:

*Female parent*.—Proprietary Spathiphyllum seedling selection identified by the code number 91-9-1, not patented.

*Male parent*.—Proprietary Spathiphyllum seedling selection identified by the code number 93-8-2, not patented.

Propagation:

*Type*.—Plant tissue culture.

*Time to produce a rooted liner*.—Summer: About 12 weeks at about 25 to 30° C. soil temperature. Winter: About 14 weeks at about 22 to 27° C. soil temperature.

Plant description:

*Growth habit*.—Medium size, round, symmetrical, relatively compact and full growth habit. Appropriate for 15-cm to 25-cm containers.

*Plant size*.—Height, soil level to top of inflorescences: About 74.0 cm. Height, soil level to top of leaf canopy: About 40.3 cm. Diameter: About 62.7 cm.

*Plant vigor*.—Moderate.

*Crop time*.—About 10 to 11 months are needed to produce a finished plant in a 15-cm container from a single tissue culture-produced microcutting.

Foliage description:

*Petiole*.—Size: About 21.2 cm long, about 6.2 mm in diameter immediately below geniculum. Geniculum: About 2.6 cm long, about 7.0 mm in diameter at the base. Petiole wings: Prominent, somewhat irregular, usually along entire petiole length, often with an apex extending past juncture with leaf blade at least on one side; usually folded adaxially, so that adaxial side of petiole and petiole wings not exposed. About 1.2 cm wide immediately below apex. Apices approximately obtuse with some acute tendencies. Color: Mature leaf, abaxial: Much darker than 147A near base. Distally lighter, similar to 147A or slightly lighter and greener than 147A immediately below geniculum. Geniculum between 146A and 147B. Petiole wings similar to 147A.

*Leaf blade*.—Shape: Broadly ovate with oval tendencies; apex acuminate with some cuspidate and aristate tendencies, often twisted; base between obtuse and attenuate, somewhat variable; base often directly connects with petiole wing at least on one side; margin entire, slightly wavy. Size: About 29.9 cm long, about 18.4 cm wide: length: width ratio about 1.6 to 1. Orientation: Approximately horizontal, except for 3 to 4 youngest leaves, which are oblique. Surface: Ribbed. Texture: Thick, leathery, glabrous, glossy; young leaves very glossy. Venation: Pinnate, prominent; midrib sunken in adaxial surface and protrudes from abaxial surface; primary veins are sunken in adaxial surface and protrude from abaxial surface. Color: Newly unrolled leaf, adaxial: Not uniform. Varies from a color slightly darker than 144A to a color slightly lighter than 147A. Newly unrolled leaf, abaxial: Varies between different combinations of 147B and 147C. Midrib approximately 144D. Mature leaf, adaxial: Much darker and a little greener than 147A. Older leaves are extremely dark and look almost black when compared against 147A. Midrib similar to or slightly darker than 147A. Mature leaf, abaxial: Approximately 147B. Midrib between 144A and 144B, except immediately above geniculum, where it is between 144A and 146A. Primary veins near midrib similar to midrib.

Inflorescence description:

*Inflorescence arrangement*.—Spathes with spadices held at a moderate distance from foliage on relatively thick and strong penduncles. Spathes cupped through senescence. Spadices in straight line with peduncle or slightly leaning forward and/or to the side.

*Flowering*.—Starts flowering naturally in spring in 15-cm containers about 14 months after planting tissue culture-produced microcuttings. At 15 months up to one inflorescence per plant.

*Spathe longevity*.—Spathe remains white for approximately 4 weeks following bud appearance and then gradually changes to a green color. Both spathe and spadix become completely green within approximately 6 weeks following bud appearance.

*Peduncle*.—Size: About 58.5 cm long and about 6.8 mm in diameter immediately below spathe. Stipe about 3.5 mm long and 6.4 mm in diameter. Color, front: A little more yellow than 147A proximally from spathe base. Between 147A and 146A distally from spathe base with short yellowish streaks on the stipe. Color, back: Varies between different combinations of 146A and 147B. Most similar to 146A between spathe base and stipe juncture. Most similar to 147B immediately proximally from spathe base.

*Spathe*.—Shape: Oval; apex acuminate with some cuspidate and/or aristate tendencies, twisted; base attenuate with long wings decurrent onto peduncle; margin entire, rolled back, especially near base. Size: About 19.6 cm long, about 10.1 cm wide; ratio length: width about 1.9 to 1. Surface: Usually smooth, often with irregular longitudinal folds and pleats. Texture: Leathery and glabrous, with pearl luster. Color: Closed bud: Darker and more yellow than 155A, greener and slightly darker than 159D. Apex approximately 144A. Most veins approximately 144B. Mature spathe, front surface: Approximately 155A. Apex between 146A and 147A. Mature spathe, back surface: Aproximately 155A. Midrib varies between 146A and 146B. Most other primary veins vary from 146A to 146D with the darkest color present near midrib in proximal half.

*Spadix*.—Shape: Cylindrical, slightly tapered towards apex; cross section approximately round. Size: About 9.8 cm long, about 2.1 cm in diameter. Flower density: About 5 to 6 flowers per linear 2 centimeters of spadix (mid-section). Color: Approximately 158B.

*Botanical flower*.—Perianth: Visible between relatively thick pistils. Pistil: Ovoid. About 6 to 7 mm long; about 3.5 mm in diameter; protrudes about 3 mm beyond perianth. Stigma relatively small. Stamens: About 3.5 mm long; cream color; flat; firmly pressed against pistil. Anthers about 2 mm long and 1 mm wide. Pollen: Not observed. Fragrance: Slight, rather unpleasant fragrance detectable in the morning.

Roots description: Thick, fleshy, cream colored main roots with yellow green root caps. Thin fibrous cream colored lateral roots.

Disease and insect resistance: Plants of 'Sthirtyone', which are grown in commercial greenhouses and shadehouses, have not shown any unusual susceptibility to pathogens or insects common to Spathiphyl lum.

I claim:

1. A new and distinct cultivar of Spathiphyllum plant named 'Sthirtyone' as described and illustrated herein.

* * * * *